United States Patent
Leavitt et al.

(10) Patent No.: US 10,557,659 B2
(45) Date of Patent: Feb. 11, 2020

(54) WEARABLE COLD PACKS UTILIZING A COOLING AGENT

(71) Applicant: FROSTY COLD, LLC, Overland Park, KS (US)

(72) Inventors: David D. Leavitt, Edmond, OK (US); John R. Bergida, Saint Charles, MO (US)

(73) Assignee: FROSTY COLD, LLC, Overland Park, KS (US)

( * ) Notice: Subject to any disclaimer, the term of this patent is extended or adjusted under 35 U.S.C. 154(b) by 151 days.

(21) Appl. No.: 15/843,218

(22) Filed: Dec. 15, 2017

(65) Prior Publication Data

US 2018/0106522 A1    Apr. 19, 2018

Related U.S. Application Data

(60) Division of application No. 14/720,593, filed on May 22, 2015, now Pat. No. 9,879,897, which is a
(Continued)

(51) Int. Cl.
*F25D 5/02* (2006.01)
*A61F 7/00* (2006.01)
(Continued)

(52) U.S. Cl.
CPC ............... *F25D 5/02* (2013.01); *A61F 7/00* (2013.01); *B01F 3/04* (2013.01); *C09K 5/066* (2013.01);
(Continued)

(58) Field of Classification Search
CPC ..................................... F25D 5/02; A61F 7/00
(Continued)

(56) References Cited

U.S. PATENT DOCUMENTS 1,313,290 A    8/1919   Ckarles
1,894,775 A    1/1933   Levenson
(Continued)

FOREIGN PATENT DOCUMENTS

CN    1056770 A     12/1991
WO    2015047564 A1   4/2015

OTHER PUBLICATIONS

U.S. Appl. No. 15/250,466, Non-Final Office Action dated Jun. 8, 2018, 39 pages.
(Continued)

*Primary Examiner* — Robert A Hopkins
(74) *Attorney, Agent, or Firm* — Lathrop Gage L.L.P.

(57) ABSTRACT

A wearable cold pack formed with a reservoir for retention of liquid, and a cooling agent composition including salt mixed with water in the reservoir. The salt having a capacity to provide an endothermic effect to enhance cooling when mixed with water. The salt material is primarily ammonium nitrate that has been stabilized against detonation by the addition of an effective amount of phosphate material. The wearable cold pack may be configured as a joint wrap, a head wrap, a neck wrap, a shoulder wrap, a helmet or many other articles. The wearable cold pack cooling agent composition is capable of cooling in the amount of at least 130 Btu/lb due to endothermic effect when mixed with water.

3 Claims, 6 Drawing Sheets

Related U.S. Application Data continuation-in-part of application No. 13/310,424, filed on Dec. 2, 2011, now Pat. No. 9,039,924.

(60) Provisional application No. 61/419,097, filed on Dec. 2, 2010.

(51) Int. Cl.
  *F24F 3/14* (2006.01)
  *B01F 3/04* (2006.01)
  *C09K 5/06* (2006.01)

(52) U.S. Cl.
  CPC ...... *F24F 3/1417* (2013.01); *F24F 2003/144* (2013.01)

(58) Field of Classification Search
  USPC .................................................. 607/110, 112
  See application file for complete search history.

(56) References Cited

U.S. PATENT DOCUMENTS

| | | |
|---|---|---|
| 1,897,723 A | 2/1933 | Free |
| 2,095,386 A | 10/1937 | Hibberd |
| 2,460,765 A | 2/1949 | Palaith |
| 2,515,840 A | 7/1950 | Rodeck |
| 2,556,893 A | 6/1951 | Zwiebach et al. |
| 2,622,415 A | 12/1952 | Landers et al. |
| 2,657,977 A | 11/1953 | Stengel et al. |
| 2,746,265 A | 5/1956 | Mills |
| 2,757,517 A | 8/1956 | Goldberg |
| 2,800,454 A | 7/1957 | Shepherd |
| 2,805,556 A | 9/1957 | Wang |
| 2,882,691 A | 4/1959 | Robbins |
| 2,900,808 A | 8/1959 | Wang |
| 2,916,866 A | 12/1959 | Brinkman |
| 2,929,220 A | 3/1960 | Schlumbohm |
| 2,968,932 A | 1/1961 | Vance et al. |
| 3,003,324 A | 10/1961 | Vance et al. |
| 3,023,587 A | 3/1962 | Robbins |
| 3,034,305 A | 5/1962 | Egidio |
| 3,058,313 A | 10/1962 | Robbins |
| 3,095,291 A | 6/1963 | Robbins |
| 3,134,577 A | 5/1964 | Wayne |
| 3,191,392 A | 6/1965 | Donnelly |
| 3,213,932 A | 10/1965 | Bernard et al. |
| 3,229,478 A | 1/1966 | Jose |
| 3,269,141 A | 8/1966 | Weiss |
| 3,309,890 A | 3/1967 | Barnett et al. |
| 3,326,013 A | 6/1967 | Jacobs |
| 3,338,067 A | 8/1967 | Warner |
| 3,366,468 A | 1/1968 | Porter |
| 3,369,369 A | 2/1968 | Weiss |
| 3,373,581 A | 3/1968 | Strader |
| 3,379,025 A | 4/1968 | Donnelly |
| 3,494,142 A | 2/1970 | Beck |
| 3,494,143 A | 2/1970 | Barnett et al. |
| 3,520,148 A | 7/1970 | Fuerle |
| 3,525,236 A | 8/1970 | Solhkhah |
| 3,559,416 A | 2/1971 | Cornwall |
| 3,597,937 A | 8/1971 | Parks |
| 3,620,406 A | 11/1971 | Evans et al. |
| 3,636,726 A | 1/1972 | Rosenfeld et al. |
| 3,726,106 A | 4/1973 | Jaeger |
| 3,759,060 A | 9/1973 | Chase |
| 3,763,622 A | 10/1973 | Stanley |
| 3,803,867 A | 4/1974 | Willis |
| 3,842,617 A | 10/1974 | Woods et al. |
| 3,852,975 A | 12/1974 | Beck |
| 3,881,321 A | 5/1975 | Riley |
| 3,889,483 A | 6/1975 | Donnelly |
| 3,919,856 A | 11/1975 | Beck |
| 3,950,158 A | 4/1976 | Gossett |
| 3,957,472 A | 5/1976 | Donnelly |
| 3,970,068 A | 7/1976 | Shotaro |
| 3,977,202 A | 8/1976 | Forusz et al. |
| 3,987,643 A | 10/1976 | Willis |
| 4,000,996 A | 1/1977 | Jordan |
| 4,010,620 A | 3/1977 | Telkes |
| 4,049,408 A | 9/1977 | Patel |
| 4,081,256 A | 3/1978 | Donnelly |
| 4,403,868 A | 9/1983 | Dieter |
| 4,462,224 A | 7/1984 | Dunshee et al. |
| 4,640,101 A | 2/1987 | Johnson |
| 4,640,264 A | 2/1987 | Yamaguchi et al. |
| 4,655,951 A | 4/1987 | Hanazaki et al. |
| 4,668,259 A | 5/1987 | Gupta |
| 4,679,407 A | 7/1987 | Kim et al. |
| 4,688,395 A | 8/1987 | Holcomb |
| 4,722,323 A | 2/1988 | Oblon |
| 4,784,678 A | 11/1988 | Rudick et al. |
| 4,816,048 A | 3/1989 | Kimmelshue |
| 4,911,740 A | 3/1990 | Schieder |
| 4,925,470 A | 5/1990 | Chou |
| 4,993,237 A | 2/1991 | Bond et al. |
| 5,184,470 A | 2/1993 | Moser et al. |
| 5,197,302 A | 3/1993 | Sabin et al. |
| 5,255,812 A | 10/1993 | Hsu |
| 5,257,755 A | 11/1993 | Moser et al. |
| 5,261,241 A | 11/1993 | Kitahara et al. |
| 5,394,703 A | 3/1995 | Anthony |
| 5,429,762 A | 7/1995 | Kitahara et al. |
| 5,431,022 A | 7/1995 | Abe |
| 5,461,867 A | 10/1995 | Scudder et al. |
| 5,626,022 A | 5/1997 | Scudder et al. |
| 5,655,384 A | 8/1997 | Joslin |
| 5,809,786 A | 9/1998 | Scudder et al. |
| 5,941,078 A | 8/1999 | Scudder et al. |
| 5,979,164 A | 11/1999 | Scudder et al. |
| 5,992,677 A | 11/1999 | Ebine |
| 6,103,280 A | 8/2000 | Molzahn et al. |
| 6,128,906 A | 10/2000 | Sillince |
| 6,141,970 A | 11/2000 | Molzahn et al. |
| 6,178,753 B1 | 1/2001 | Scudder et al. |
| 6,233,945 B1 | 5/2001 | Kohout |
| 6,266,879 B1 | 7/2001 | Scudder et al. |
| 6,351,953 B1 | 3/2002 | Scudder et al. |
| 6,367,277 B1 | 4/2002 | Kinkel |
| 6,722,153 B2 | 4/2004 | Jeuch |
| 6,739,731 B2 | 5/2004 | Katzman |
| 6,789,391 B2 | 9/2004 | Graham et al. |
| 6,827,080 B2 | 12/2004 | Fish et al. |
| 6,854,280 B2 | 2/2005 | Jeuch |
| 6,962,149 B2 | 11/2005 | Kolb |
| 6,986,345 B2 | 1/2006 | Kolb |
| 7,004,161 B2 | 2/2006 | Kolb |
| 7,025,055 B2 | 4/2006 | Scudder et al. |
| 7,117,684 B2 | 10/2006 | Scudder et al. |
| 7,240,507 B2 | 7/2007 | Jeuch |
| 7,350,361 B2 | 4/2008 | Maxwell et al. |
| 7,350,362 B2 | 4/2008 | Danwoody |
| 7,390,341 B2 | 6/2008 | Jeuch |
| 7,681,726 B2 | 3/2010 | O'Donnell et al. |
| 8,585,358 B2 | 11/2013 | Matsuo et al. |
| 8,826,672 B2 | 9/2014 | Farone et al. |
| 9,770,061 B2* | 9/2017 | Sansone .............. A42B 3/285 |
| 2002/0177886 A1 | 11/2002 | Sharma et al. |
| 2004/0167456 A1 | 8/2004 | Kingsford et al. |
| 2012/0138848 A1 | 6/2012 | Leavitt et al. |
| 2012/0245662 A1* | 9/2012 | Page .................... A61F 7/106 607/112 |
| 2015/0297396 A1* | 10/2015 | Whitely .............. A61F 7/106 607/114 |

OTHER PUBLICATIONS

U.S. Appl. No. 15/250,466, Notice of Allowance dated Aug. 6, 2018, 8 pages.

PCT Application No. US2015/047564, International Search Report and Written Opinion dated Dec. 10, 2015, 7 pages.

\* cited by examiner

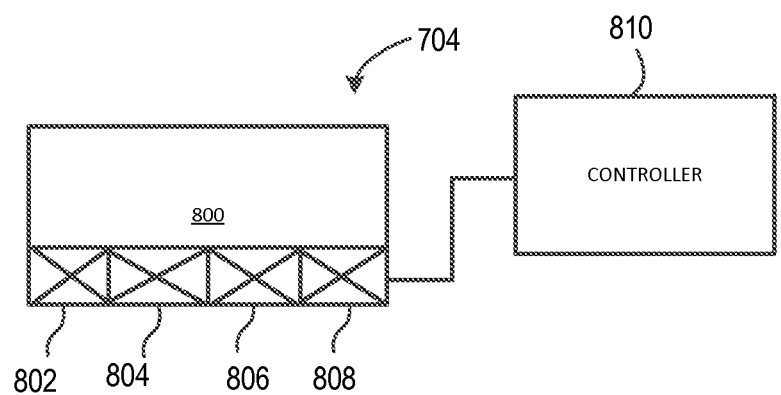
FIG. 8
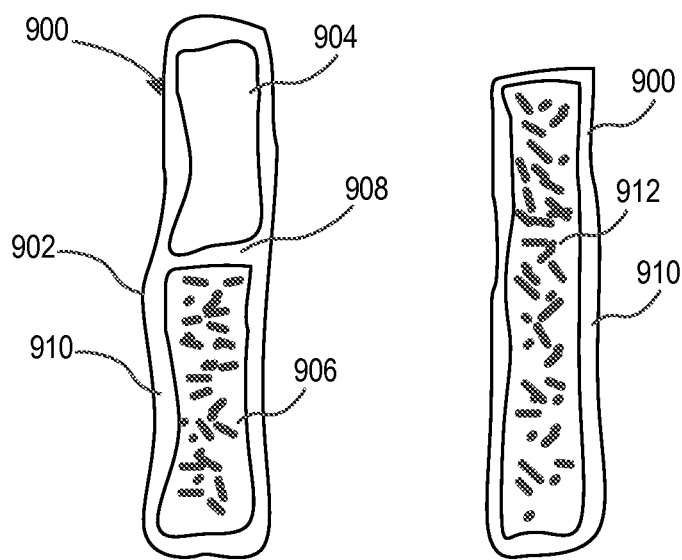 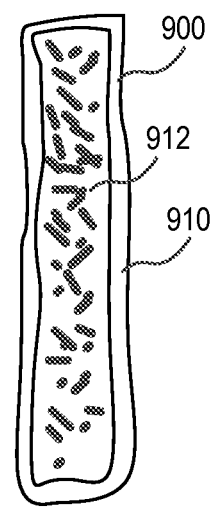
FIG. 9A  FIG. 9B

WEARABLE COLD PACKS UTILIZING A COOLING AGENT

RELATED APPLICATION

This application is a divisional application of Ser. No. 14/720,593 filed on May 22, 2015 which is a continuation-in-part of application Ser. No. 13/310,424 filed Dec. 2, 2011, now U.S. Pat. No. 9,039,924, issued May 26, 2015, which claims priority to U.S. Patent Application 61/419,097, filed Dec. 2, 2010, the disclosures of which are incorporated by reference to the same extent as though fully replicated herein.

BACKGROUND OF THE INVENTION

1. Field of the Invention

This invention relates generally to wearable cold packs containing cooling agents or compositions that can be used to cool surfaces, liquids and solids when activated upon mixing with water and more particularly relating to cooling agents that are effective, resistant to combustion, insensitive to detonation, non-toxic and recyclable as a balanced NPK fertilizer.

2. Description of the Art

The present invention relates to wearable cold packs containing compositions which produce an endothermic reaction when mixed with water, and which are non-toxic, non-explosive and can be recycled as a balanced NPK fertilizer when no longer useful as a cooling agent. Although not so limited, the invention has particular utility when used as a cooling agent in therapeutic cold packs for the treatment of sprains and injuries; for chilling of beverages and packaged foods; and for other applications where it is desirable to cool surfaces, fluids or objects.

Compositions producing an endothermic effect and devices or containers that utilize such compositions are known in the prior art. Such compositions typically produce their endothermic effect by either chemical reaction or by heat absorbing processes. Examples of endothermic chemical reactions include: the reaction of barium hydroxide octahydrate crystals with dry ammonium chloride with the subsequent evolution of ammonia; the reaction of thionyl chloride with cobalt(II) sulfate heptahydrate; and the reaction of ethanoic acid with sodium carbonate. Examples of such endothermic processes include: melting ice cubes, melting solid salts, evaporating liquid water, making an anhydrous salt from a hydrate and the dissolution of salts in water.

As a general rule, compositions that undergo endothermic reactions are useful for cooling but often utilize toxic reactants such as cobalt and barium hydroxide or produce noxious and irritating byproducts such as ammonia, or gasses that are difficult to contain and process such as carbon dioxide. Heat-absorbing processes are thus more commonly used to cool substances compared to chemical reactions. With respect to cold packs and beverage coolers, heat-absorbing processes based upon the dissolution of various salts in water are commonly described. Here the selection of a particular material has primarily been based upon the magnitude of its positive enthalpy of solution (heat of solution) and its solubility in water or another solvent whereby the most effective compositions have the highest positive heat of solution and highest solubility.

With respect to the above, U.S. Pat. No. 1,894,775 disclosed the use of various sodium, potassium and ammonium salt solutions, including sodium acetate, ammonium nitrate and sodium thiosulfate mixed with water, to provide therapeutic cooling in 1933. Subsequently many other patents have disclosed the use of additional compounds along with various wetting and gelling agents and co-solvents other than water to improve the cooling performance of endothermic compositions when applied to cold packs and beverages. As an example, U.S. Pat. No. 3,957,472 describes a chemical heat transfer unit that uses compounds selected from a group that includes ammonium sulfamate, potassium nitrate, ammonium bisulfate, ammonium bromide, ammonium bicarbonate, ammonium iodide, ammonium magnesium selenate, ammonium maganese sulfate, ammonium phosphate dibasic, ammonium potassium tartrate, ammonium salicylate, ammonium sulfate, ammonium sodium sulfate, ammonium thiocyonate, ammonium persulfate, potassium phosphate, potassium sulfate, potassium sodium tartrate, potassium thiocyanate, potassium iodide, potassium chloride, urea, afenil, sodium acetate, sodium citrate, sodium nitrate, sodium thiocyanate, sodium thiosulfate, citric acid, tartaric acid, ferric ammonium sulfate and thiourea. In another example, U.S. Pat. No. 4,081,256 describes an endothermic composition and cold pack whereby urea, hydrated sodium acetate, potassium chloride, potassium nitrate, ammonium chloride, and guar gum are blended together to extend the cooling life of the cold pack. In still other examples, U.S. Pat. No. 4,010,620 utilizes ammonium chloride and ammonium nitrate for maximum cooling effect; U.S. Pat. No. 6,233,945 describes an extended life cold pack that uses ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, and combinations thereof; U.S. Pat. No. 5,429,762 discloses a cooling agent consisting of one or more of a group comprised of disodium hydrogen phosphate, sodium dihydrogen phosphate, trisodium phosphate, sodium ammonium hydrogen phosphate, diammonium hydrogen phosphate, and hydrates thereof; and U.S. Pat. No. 4,010,620 describes a cooling system that utilizes sodium nitrate, ammonium nitrate, ammonium thiocyanate, potassium thiocyanate, and ammonium nitrate individually or in combination.

A review of the prior art reveals that, although a wide variety of chemical compositions have been disclosed, only a select few are preferred based upon performance as a cooling agent.

Chemical cooling agents also suffer from the stigma of being a wasteful product that is not easily reused or recycled. Many of the endothermic compounds and compositions shown in Table 1 or disclosed in the prior art are classified as hazardous substances or are harmful to the environment if disposed in an improper or imprudent manner after they no longer have utility as a cooling agent.

For all of the above reasons, cooling agents and compositions described in the prior art have had limited commercial success with the possible exception of cold pack applications. The most effective commercialized cold pack applications, however, utilize ammonium nitrate or mixtures of ammonium nitrate and urea and are susceptible to increased regulation and subject to restrictions on use, and may not be available for use in consumer products in the future.

SUMMARY

It is a principal object of this invention to provide a wearable cold pack that utilizes safe, non-toxic and recyclable cooling compositions comprising solid particulate compounds that undergo an effective endothermic process when mixed with water such that the resulting mixture is useful for cooling surfaces, liquids and solids. Because ammonium nitrate and urea are already in commercial use for cold pack applications but are in danger of being rendered unmarketable because of concerns about safety and explosivity, it is also an object of the invention to provide safe and non-explosive endothermic compositions that contain these compounds and the other strongly oxidizing cooling agents described herein. It is also an object of this invention to provide endothermic compositions that can be recycled for a beneficial use as balanced NPK fertilizer when they are no longer useful as cooling agents.

Although not prescribed for various cooling agents, methods for improving the safety of ammonium nitrate for use as a fertilizer are described in the prior art. For example, U.S. Pat. No. 3,366,468 disclosed a method for manufacturing desensitized ammonium nitrate having lowered flammability and reduced sensitivity to explosive detonation. Here various ammonium phosphate compounds are incorporated together with ammonium nitrate during process of manufacturing ammonium nitrate fertilizer. The resultant ammonium nitrate fertilizer containing 1% to 5% ammonium phosphate was desensitized to explosion and was rendered non-explosive when containing more than 5% ammonium phosphate. U.S. Pat. No. 6,130,139 discloses the use of ammonium phosphate compounds including ammonium polyphosphate as a barrier coating applied to ammonium nitrate prills that reduces the efficacy of the prills as oxidizing agents.

The present invention combines various ammonium phosphate compounds that are known to suppress flame formation and explosivity and act as fire retardants with the preferred and strongly oxidizing compounds described in Table 1 such that these compounds are rendered non-explosive and resistant to combustion. Unlike the methods disclosed in the prior art, the ammonium phosphate compounds used in this invention do not have to be incorporated with ammonium nitrate or other oxidizing agents during the manufacture of fertilizer or used to coat prills in order to be effective. The selected compounds can simply be blended together to form an intimate mixture when used to prepare a cooling composition. Compositions used in this invention that contain ammonium phosphate compounds along with strongly oxidizing endothermic compounds remain safe and non-explosive even though blended with carbon containing compounds that are known to form explosive mixtures with compounds such as ammonium nitrate. This safety feature is useful for compositions that are used in cold packs, since such cold pack products often contain carbon-based gels and thickening agents such as guar gum, xanthates and carboxymethylcellulose.

When prepared in this manner, the ammonium phosphate compounds, and especially ammonium polyphosphate, also improve the stability and lengthen the shelf-life of mixtures of urea and ammonium nitrate. Mixtures of urea and ammonium nitrate are destabilized by acidic hydrolysis of the urea to form free water which can prematurely solubilize ammonium nitrate during storage. Ammonium polyphosphate is hydroscopic and is thought to act as a scavenger of any free water that might form during the storage of ammonium nitrate/urea mixtures, thus preventing the water from dissolving ammonium nitrate. Urea is also destabilized by other endothermic compounds besides ammonium nitrate when mixed together, and ammonium polyphosphate can also be an effective stabilizer of such mixtures.

With the current social and political trends favoring sustainability and protection of the environment, chemical products that are non-toxic and can be reused or recycled or disposed of without contributing to pollution and waste are greatly preferred over non-recyclable products. The primary emphasis in the prior art is the disclosure of endothermic compounds that are effective cooling agents with little regard for toxicity of the compounds or their reuse or disposal. The use of a spent cooling agent as fertilizer or plant growth regulator is sometimes mentioned but only as a secondary benefit, primarily with respect to cooling agents that utilize urea, ammonium nitrate, potassium nitrate, ammonium sulfate with attention paid to nitrogen-containing compounds that can be used as nitrogen-containing fertilizers.

In this present invention, effective endothermic compositions are described that can be reused as a balanced fertilizer containing nitrogen (N), phosphorus (P), and potassium (K) because only balanced fertilizers contain all of the essential primarily nutrients necessary for plant growth. Such compositions have greater residual value compared to solutions that contain only nitrogen or only nitrogen and potassium and are more useful to the end-user and more likely to be reused and recycled instead of being disposed of as a waste material when no longer effective as a coolant.

Compositions in accordance with this invention thus comprise cooling agents that always include one or more compounds from a group consisting of endothermic compounds shown in Table 1 that contain potassium; one or more compounds from a group of endothermic compounds shown in Table 1 that contain nitrogen; and at least one compound from a group consisting of ammonium phosphate, diammonium phosphate, ammonium polyphosphate, ammonium pyrophosphate and ammonium metaphosphate such that the compound or mixture of compounds in this group is at least 1% by weight of the final composition. The compositions may also include one or more compounds from a group comprising sodium perchlorite ($NaClO_3$), sodium perchlorate ($NaClO_4$), sodium bromate dehydrate ($NaBr.2H_2O$), sodium acetate trihydrate ($NaC_2H_3O_2.3H_2O$), sodium thiosulfate ($Na_2S_2O_3$), sodium thiosulfate pentahydrate ($Na_2S_2O_3.5H_2O$), trisodium phosphate ($Na_3PO_4$), and sodium bicarbonate ($NaHCO_3$) and about 0.5 to 1% thickening agent comprising guar gum, xanthate gum, carboxymethylcellulose, or mixtures thereof. The compositions when mixed with water at around 20° C. attain a temperature of around 10° C. or less within 60 seconds after mixing and can be recycled for use as a balanced NPK fertilizer when no longer useful as a coolant.

In one aspect, a cooling system, such as an evaporative cooling system, may be improved by the use of these cooling agent compositions. A salt-based cooling agent composition is crystallized onto an evaporative support. The salt material has a capacity to provide an endothermic effect that enhances cooling when mixed with water. A means, such as a mixer, sprayer or nozzle, is provided for mixing the cooling agent composition with water to provide the endothermic effect. A means is also provided for recycling the salt material for recrystallization on the evaporative support. This second means may be a controller that governs operation of the mixer sprayer or nozzle to enhance the crystallization process under the influence of flowing air.

In one aspect, the cooling agent composition may be primarily ammonium nitrate that has been stabilized against detonation by the addition of an effective amount of phosphate material. There may be added also additional salts to form an industry recognized NPK blend, such that the cooling agent composition at the end of its use may be discarded by use as a fertilizer. Cooling agent compositions of this nature, when in substantially complete crystallized form, may be formulated to provide at least about 130 Btu/lb from the effects of endothermic activity when mixed with water.

In one aspect, the cooling system may be constructed and arranged for the cooling of a building area selected from the group consisting of a house, a data center, a computer room, and an industrial facility. Alternatively, the evaporative cooling may be constructed and arranged as a cooling tower selected from the group consisting of a counterflow tower and a crossflow tower.

In one aspect, the cooling system may be constructed and arranged for specialty uses, such as emergency use or permanent use in the cooling of bearings on a solar wind turbine. These bearings and an associated braking system may otherwise overheat, especially in the event of high winds. The cooling system may be constructed and arranged for the cooling of a solar panel, or an industrial cooling tower.

In other aspects, the cooling agent composition is provided in a wearable cold pack. This may be formed as a wearable article of clothing formed with a reservoir for retention of liquid. The cooling agent composition including salt mixed with water provides cooling activity in the reservoir. The wearable cold pack may be, for example, constructed and arranged as such articles a joint wrap, head wrap, neck wrap, shoulder wrap or helmet.

BRIEF DESCRIPTION OF THE DRAWINGS

FIG. 8 shows a distribution basin that may be suitably used in the embodiment of FIG. 7;

FIG. 9A is a cold pack capable of utilizing the endothermic action of a cooling agent composition according to one embodiment;

FIG. 9B shows the cooling pack with water and salt constituents mixed to provide endothermic action.

DESCRIPTION OF THE PREFERRED EMBODIMENTS OF THE INVENTION

Figure 1:
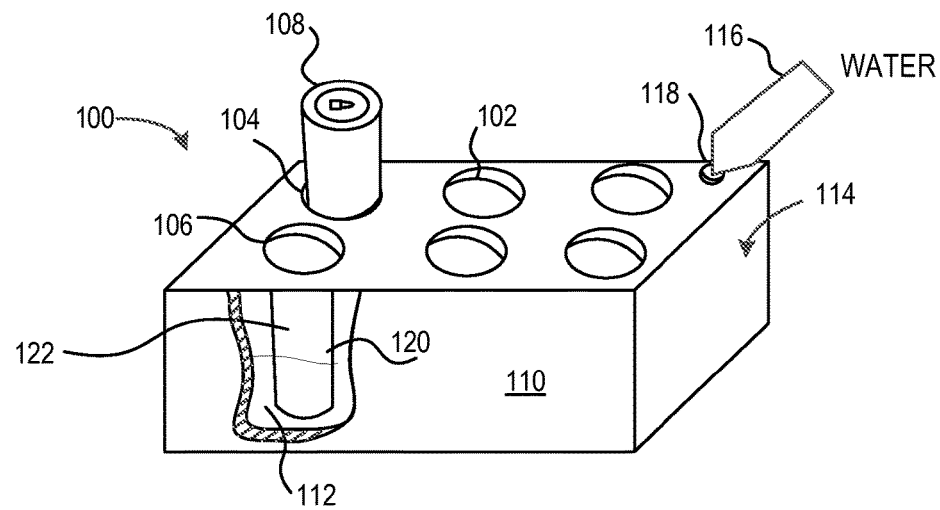
FIG. 1 shows a cooler that may be used to chill beverages by the endothermic action of a cooling agent composition.

This is best illustrated by a review of the selected endothermic compounds shown in Table 1.

TABLE 1

SELECTED ENDOTHERMIC COMPOUNDS USEFUL FOR COOLING SURFACES, SOLIDS AND LIQUIDS

| Solute | MW (gm/mol) | $LD_{50}$ (oral-rat; mg/kg) | Heat of Solution (kJ/mol) | Solubility (gm solute per 100 gm water at 20° C.) | Heat Absorbed (during dissolution of compound in 100 gm of water at 25° C. in kJ) | Theoretical Change in Temperature of a saturated solution (° C.) | Predicted Change in Temperature of a saturated solution exhibiting 30% heat loss (° C.) | Predicted Final Temperature of 255 gm of liquid exposed to saturated solution exhibiting 50% heat loss (° C.) |
|---|---|---|---|---|---|---|---|---|
| $C_{12}H_{22}O_{11}$ | 342.3 | 29700 | 5.4 | 201.9 | 3.19 | 3 | 2 | 24 |
| $C_6H_{12}O_6$ | 180.16 | 25800 | 11 | 49 | 2.99 | 5 | 3 | 24 |
| $C_6H_{12}O_6 \cdot H_2O$ | 198.16 | 25800 | 19 | 49 | 4.70 | 8 | 5 | 23 |
| $CO(NH_2)_2$ | 60.07 | 8471 | 15 | 108 | 26.97 | 31 | 22 | 16 |
| $KF \cdot 2(H_2O)$ | 94.13 | 245 | 6.97 | 349 | 25.84 | 14 | 10 | 17 |
| KCl | 74.55 | 2600 | 17.22 | 34.2 | 7.90 | 14 | 10 | 22 |
| $KClO_3$ | 122.55 | 1870 | 41.38 | 7.3 | 2.46 | 5 | 4 | 24 |
| $KClO_4$ | 138.54 | 100 | 51.04 | 1.5 | 0.55 | 1 | 1 | 25 |
| KBr | 119 | 3070 | 19.87 | 65.3 | 10.90 | 16 | 11 | 21 |
| $KBrO_3$ | 106 | 321 | 41.13 | 6.91 | 2.68 | 6 | 4 | 24 |
| KI | 166 | 1862 | 20.33 | 140 | 17.15 | 17 | 12 | 19 |
| $KIO_3$ | 214 | 136 | 27.74 | 4.74 | 0.61 | 1 | 1 | 25 |
| $KNO_2$ | 85.11 | 250 | 13.35 | 306 | 48.00 | 28 | 20 | 17 |
| $KNO_3$ | 101.1 | 3750 | 34.89 | 31.6 | 10.91 | 20 | 14 | 21 |
| $K_2S_2O_3 \cdot 5H_2O$ | 360.32 | 802 | 47 | 205 | 26.74 | 21 | 15 | 16 |
| KCN | 65.12 | 5 | 11.72 | 71.6 | 12.89 | 18 | 13 | 21 |
| KCNO | 81.12 | 841 | 20.25 | 75 | 18.72 | 26 | 18 | 19 |
| KCNS | 97.18 | 854 | 24.23 | 224 | 55.85 | 41 | 29 | 7 |
| $KMnO_4$ | 158.04 | 1090 | 43.56 | 6.3 | 1.74 | 4 | 3 | 24 |
| $K_2SO_4$ | 174.25 | 6600 | 23.8 | 11.1 | 1.52 | 3 | 2 | 25 |
| NaF | 41.99 | 52 | 0.91 | 4.13 | 0.09 | 0 | 0 | 25 |
| NaCl | 58.44 | 3000 | 3.88 | 359 | 23.84 | 12 | 9 | 17 |

TABLE 1-continued

SELECTED ENDOTHERMIC COMPOUNDS USEFUL FOR COOLING SURFACES, SOLIDS AND LIQUIDS

| Solute | MW (gm/mol) | $LD_{50}$ (oral-rat; mg/kg) | Heat of Solution (kJ/mol) | Solubility (gm solute per 100 gm water at 20° C.) | Heat Absorbed (during dissolution of compound in 100 gm of water at 25° C. in kJ) | Theoretical Change in Temperature of a saturated solution (° C.) | Predicted Change in Temperature of a saturated solution exhibiting 30% heat loss (° C.) | Predicted Final Temperature of 255 gm of liquid exposed to saturated solution exhibiting 50% heat loss (° C.) |
|---|---|---|---|---|---|---|---|---|
| $NaClO_2$ | 90.44 | 165 | 0.33 | 39 | 0.14 | 0 | 0 | 25 |
| $NaClO_2 \cdot 3H_2O$ | 144.44 | 165 | 28.58 | 39 | 7.72 | 13 | 9 | 22 |
| $NaClO_3$ | 106.44 | 1200 | 21.72 | 101 | 20.61 | 25 | 17 | 18 |
| $NaClO_4$ | 122.44 | 2100 | 13.88 | 201 | 22.79 | 18 | 13 | 18 |
| $NaClO_2 \cdot H_2O$ | 140.44 | 2100 | 22.51 | 201 | 32.22 | 26 | 18 | 14 |
| $NaBr \cdot 2H_2O$ | 138.89 | 3500 | 18.64 | 90.5 | 12.15 | 15 | 11 | 21 |
| $NaBrO_3$ | 150.89 | 301 | 26.9 | 37.4 | 6.67 | 12 | 8 | 23 |
| $NaI \cdot 2H_2O$ | 185.89 | 4340 | 16.13 | 184 | 15.97 | 13 | 9 | 20 |
| $NaIO_3$ | 197.89 | 180 | 20.29 | 9.47 | 0.97 | 2 | 1 | 25 |
| $NaNO_2$ | 68 | 180 | 13.89 | 80.8 | 16.50 | 22 | 15 | 20 |
| $NaNO_3$ | 84.99 | 3236 | 20.5 | 87.6 | 21.13 | 27 | 19 | 18 |
| $NaC_2H_3O_2 \cdot 3H_2O$ | 136.08 | 3530 | 19.66 | 85 | 12.28 | 16 | 11 | 21 |
| $Na_2S_2O_3 \cdot 5H_2O$ | 248.17 | 2300 | 47.4 | 79 | 15.09 | 20 | 14 | 20 |
| NaCN | 49 | 6 | 1.21 | 58 | 1.43 | 2 | 2 | 25 |
| $NaCN \cdot 2H_2O$ | 85 | 6 | 18.58 | 82 | 17.92 | 24 | 16 | 19 |
| NaCNO | 65.01 | 5 | 19.2 | 110 | 32.49 | 37 | 26 | 14 |
| NaCNS | 81.05 | 764 | 6.83 | 139 | 11.71 | 12 | 8 | 21 |
| $Na_3PO_4$ | 163.94 | 7400 | 15.9 | 8.8 | 0.85 | 2 | 1 | 25 |
| $NaHCO_3$ | 83.99 | 4220 | 16.7 | 7.8 | 1.55 | 3 | 2 | 24 |
| $NH_4Cl$ | 53.49 | 1650 | 14.78 | 29.7 | 8.21 | 15 | 11 | 22 |
| $NH_4ClO_4$ | 117.49 | 100 | 33.47 | 20.8 | 5.93 | 12 | 8 | 23 |
| $NH_4Br$ | 97.94 | 2700 | 16.78 | 78.3 | 13.42 | 18 | 13 | 21 |
| $NH_4I$ | 144.94 | 76 | 13.72 | 172 | 16.28 | 14 | 10 | 20 |
| $NH_4IO_3$ | 192.94 | 500 | 31.8 | 182 | 30.00 | 25 | 18 | 15 |
| $NH_4NO_2$ | 64.04 | 57 | 19.25 | 150 | 45.09 | 43 | 30 | 10 |
| $NH_4NO_3$ | 80.06 | 2217 | 25.69 | 150 | 48.13 | 46 | 32 | 9 |
| $NH_4CN$ | 44.06 | 525 | 17.57 | 60 | 23.93 | 36 | 25 | 17 |
| $NH_4CNS$ | 76.12 | 954 | 22.58 | 144 | 42.72 | 42 | 29 | 11 |
| $(NH_4)_3PO_4$ | 149 | 3000 | 14.45 | 37.7 | 3.66 | 6 | 4 | 24 |
| $CH_3NH_3Cl$ | 67.52 | 1600 | 5.77 | 30.6 | 2.61 | 5 | 3 | 24 |
| $AgClO_4$ | 207.32 | Toxic | 7.38 | 557 | 19.83 | 7 | 5 | 18 |
| $AgNO_2$ | 153.87 | Toxic | 36.94 | 4.2 | 1.01 | 2 | 2 | 25 |
| $AgNO_3$ | 169.87 | Toxic | 22.59 | 257 | 34.18 | 23 | 16 | 14 |
| $RbClO_4$ | 184.92 | 3310 | 56.74 | 1.3 | 0.40 | 1 | 1 | 25 |
| $RbNO_3$ | 147.47 | 4625 | 36.48 | 44.28 | 10.95 | 18 | 13 | 21 |
| $CsClO_4$ | 232.36 | 3310 | 55.44 | 1.97 | 0.47 | 1 | 1 | 25 |
| $CsNO_3$ | 194.91 | 1200 | 40 | 9.16 | 1.88 | 4 | 3 | 24 |
| $BaCl_2 \cdot 2H_2O$ | 244.27 | 118 | 20.58 | 31 | 2.61 | 5 | 3 | 24 |
| $MgSO4 \cdot 7H2O$ | 246.36 | 2840 | 16.11 | 255 | 16.67 | 11 | 8 | 20 |

In Table 1, the selected endothermic compounds (solutes) are classified with respect to their toxicity, heat of solution and solubility in water. Toxicity is measured by the oral rat $LD_{50}$ value for a compound taken from various toxicological databases or from the Material Safety Data Sheet (MSDS) for the compound or from other indicators of toxicity if $LD_{50}$ data isn't available. Compounds with an $LD_{50}$ above 1000 are preferred for applications where there is a potential for human and environmental exposure. Heat of solution values are taken from *CRC Handbook of Chemistry and Physics, 90th Ed.* Solubility values are taken from the Solubility Database shown on the International Union of Pure and Applied Chemistry/National Institute of Standards and Technology website.

An endothermic process absorbs heat from the environment during the dissolution of the compound in water. The theoretical heat absorbed during the dissolution of compound in 100 gm of water at 25° C. in kJ can be calculated from the following equations using the data in the table:

$$[H_{Sol}]*[\text{moles of solute}]=[\text{mass of solution}]*C_p*[T_1-T_2] \quad 1.$$

where $H_{Sol}$ is in kJ/Mol
mass of solution refers to the mass of a saturated solution in 100 gm of water
$C_p$ is assumed to be 4.184 J/g° C.
$T_1$ is 20° C.
$T_2$ is the final temperature of the saturated solution $$\Delta q=\text{heat absorbed}=[\text{mass of solution}]*4.184*[T_1-T_2] \quad 2.$$

The theoretical heat absorbed and the final theoretical temperature of the saturated endothermic solutions are shown in the table.

This data was then used to predict the cooling effect of saturated solutions of the various endothermic compounds upon a typical beverage container having a volume of around 12 ounces. For a reference, approximately 60 grams of 200 mesh ammonium nitrate was thoroughly mixed with approximately 50 grams of water in an un-insulated 100 ml sealed container which was then placed in a larger sealed un-insulated container having a volume of around 360 ml that contained around 255 ml of water. The larger sealed container had approximately the same dimensions and surface area as a typical 12 ounce beverage can. After around 30 seconds, the temperature of the saturated solution in the 100 ml container attained −7° C. from an initial temperature of 25° C. and after around 3 minutes the temperature of the water in the 360 ml container attained around 9° C. from an initial temperature of 25° C. This reference test indicated that the theoretical change in temperature of a saturated solution of ammonium nitrate was approximately 30% more than the measured change in temperature due to heat losses from the 100 ml container while the container was being mixed prior to placing it in the 360 ml container that contained the water. A similar calculation showed that heat losses from the un-insulated 360 ml container was around 50%. The heat loss factors were then used to determine the predicted temperature changes shown in the table for the various saturated salt solutions and for a 360 ml container filled with 255 ml of liquid exposed to the various saturated salt solutions. The predicted results were then used to rate the performance of the selected endothermic compounds in terms of their performance as a cooling agent.

The compounds predicted in the table to be most useful as cooling agents should show at least a 10° C. reduction in temperature when dissolved in water and include urea ($CO(NH_2)_2$), potassium fluoride dihydrate ($KF.2(H_2O)$), potassium chloride (KCl), potassium bromide (KBr), potassium iodide (KI), potassium nitrite ($KNO_2$), potassium nitrate ($KNO_3$), potassium thiosulfate pentahydrate ($K_2S_2O_3.5H_2O$), potassium cyanide (KCN), potassium cyanate (KCNO), potassium thiocyanide (KCNS), sodium perchlorite ($NaClO_3$), sodium perchlorate ($NaClO_3$), sodium perchlorite dihydrate ($NaClO_2.H_2O$), sodium bromide dihydrate ($NaBr.2H_2O$), sodium nitrite ($NaNO_2$), sodium nitrate ($NaNO_3$), sodium acetate trihydrate ($NaC_2H_3O_2.3H_2O$), sodium thio sulfate pentahydrate ($Na_2S_2O_3.5H_2O$), sodium cyanide dihydrate ($NaCN.2H_2O$), sodium cyanate (NaCNO), ammonium chloride ($NH_4Cl$), ammonium bromide ($NH_4Br$), ammonium iodide ($NH_4I$), ammonium iodate ($NH_4IO_3$), ammonium nitrite ($NH_4NO_2$), ammonium nitrate ($NH_4NO_3$), ammonium cyanide ($NH_4CN$), ammonium thiocyanide ($NH_4CNS$), silver nitrate ($AgNO_3$) and rubidium nitrate ($RbNO_3$).

Of this group, potassium fluoride dehydrate, potassium nitrite, potassium thiosulfate pentahydrate, potassium cyanide, potassium cyanate, potassium thiocyanide, sodium nitrite, sodium cyanide dihydrate, sodium cyanate, ammonium iodide, ammonium iodate, ammonium nitrite, ammonium cyanide, ammonium thiocyanide, and silver nitrate have $LD_{50}$ values below 1000 or are toxic and are less than desirable for use in a consumer-oriented product such as a cold pack or beverage coolant. Potassium nitrite, potassium nitrate, sodium perchlorite, sodium perchlorate, sodium perchlorite dihydrate, sodium nitrite, sodium nitrate, ammonium nitrite and ammonium nitrate are all strong oxidizing agents and thus are reactive and have a tendency to promote combustion or are unstable during storage. Urea is also described as being unstable when mixed or blended with a wide variety of other endothermic compounds including ammonium nitrate, and blends of urea and other compounds that are described in the prior art as having synergistic coolant properties are rendered ineffective by a reduced shelf-life. Potassium nitrite, potassium nitrate, sodium nitrate, ammonium nitrite and ammonium nitrate are also capable of detonation and explosion, with ammonium nitrate having a particularly bad reputation as the explosive of choice for weapons of terror even though it is one of the most effective cooling agents disclosed in Table 1 and in the prior art. Mixtures of ammonium nitrate and urea are also commonly formulated together to make powerful commercial explosives.

A preferred composition within the broad ranges set forth above, which exhibits an optimum combination of properties, consists essentially of compounds or blends of compounds: (1) such that the mixture contains nitrogen, phosphorus and potassium (NPK); (2) such that the mixture shows at least a 14° C. drop in temperature when mixed with water; and (3) that are non-toxic or have an $LD_{50}$ greater than 1000. In one aspect, the preferred composition is thus selected from a group consisting of urea, potassium nitrate, potassium thiosulfate pentahydrate, sodium nitrate, ammonium nitrate, ammonium phosphate ammonium polyphosphate, and combinations thereof. In parts by weight, the preferred composition contains about 50 to 95 parts ammonium nitrate; about 0 to 50 parts urea; about 0 to 50 parts sodium nitrate; about 4 to 30 parts potassium nitrate or potassium thiosulfate pentahydrate; and between 1 and 10 parts ammonium phosphate or ammonium polyphosphate. Preferably about 90 parts by weight water are added to this composition to initiate the endothermic reaction.

Although the particle size of the various components of the composition can vary depending upon the application, the components must be blended together to create an intimate mixture whereby the particles of ammonium phosphate or polyphosphate are in very close contact or proximity to the particles of urea, potassium nitrate, sodium nitrate and ammonium nitrate. To that end, the components of the composition are typically co-milled together to create an intimate mix having an average particle size of at least 100 mesh and preferably greater than 200 mesh.

For example, a cooling agent composition that is useful for cold packs contains 50 parts ammonium nitrate, 40 parts urea, 4 parts potassium nitrate, 5 parts ammonium polyphosphate and around 1 part guar gum or xanthate powder added as a thickening agent. The mixture of components is co-milled to form a 100 mesh powder that when mixed with around 90 parts water is effective to reduce the temperature of the mixture by around 20° C. within 120 seconds after dissolution of the components and can maintain cooling of a surface for at least 15 minutes. The dry-milled cooling agent composition is stable, non-toxic, non-explosive and safe to use as a consumer product. The saturated solution containing the cooling agent composition forms a balanced NPK liquid fertilizer having an NPK ratio of 42-1.4-1.6.

As another example, a cooling agent composition that is useful for chilling canned or bottled beverages contains 90 parts ammonium nitrate, 5 parts potassium nitrate and 5 parts ammonium phosphate. The mixture of components is co-milled to form a 200 plus mesh powder that when mixed with around 90 parts water is effective to reduce the temperature of the mixture by around 30° C. within 60 seconds after dissolution of the components and can be used to rapidly cool a beverage where rapidity of cooling is more important than maintaining a cooling effect. The dry-milled cooling agent composition is non-toxic, non-explosive and safe to use as a consumer product. The saturated solution containing the cooling agent composition forms a balanced NPK liquid fertilizer having an NPK ratio of 32-1.4-2.

The cooling agent composition described above may be used in a variety of applications. In one aspect, FIG. 1 shows a cooler 100 with a plurality of open cylinders 102, 104, 106 for receipt of a beverage, such as beverage 108. Wall 110 is shown with a breakaway section for purposes of illustration to reveal an interior chamber 112 enclosed by shell 114. The shell 114 is preferably made of a waterproof insulating material, such as Styrofoam or plastic encased styrofoam. As shown in FIG. 1, water 116 is being poured through opening 118 for mixing with the cooling agent composition. The mixture is rising to level 120 and will eventually cover the exterior surface of cylinder sleeve 122. The cylinder sleeve 122 may be made, for example, out of plastic that is more conductive to heat than is the shell 114, because it is desirable to enhance heat transfer for purposes of cooling beverages.

It will be appreciated that cooler 100 is shown as a beverage cooler, but the cylinders 102, 104, 106 may be made with changed dimensions complementary to any number of other items that may require cooling in circumstances, for example, where there may be a lack of refrigeration. The cooler as shown may therefore, be adapted to cool blood, blood plasma, dialysis materials, vaccines, or organs for transplant, or food products such as milk or ice cream. The cooler 100 may even be formed as a coolant reservoir for an ice cream maker, or as a slushie or daiquiri maker.

Figure 2:
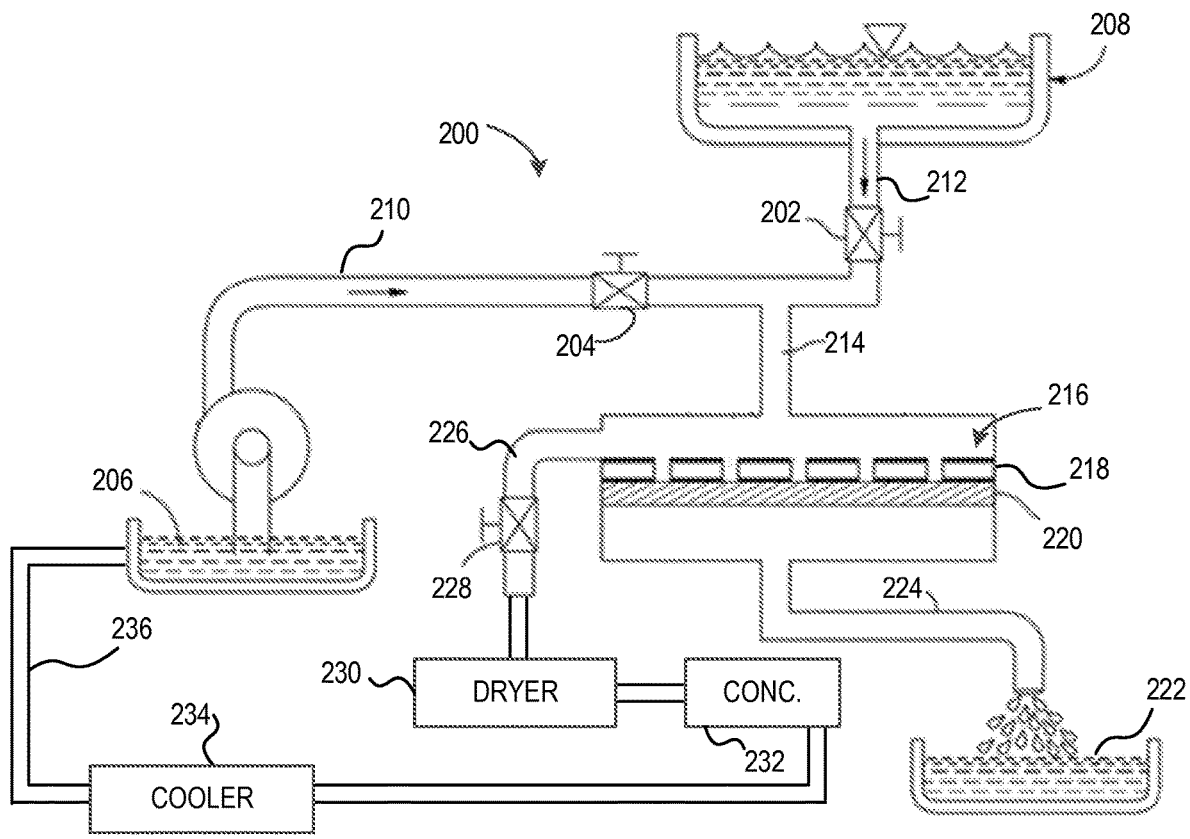
FIG. 2 is a system schematic drawing of a cooling system utilizing the endothermic action of a cooling agent composition.

FIG. 2 shows a cooling system 200 that may be used in applications including food service, commercial refrigeration, chillers for use in machinery or plants, dialysis and medical equipment, dehumidifiers, computers, data centers, or air conditioning units. Valves 202, 204 may be used for selective isolation of corresponding salt water reservoirs 206, 208 on lines 210, 212. Flow through line 214 communicates salt water to membrane filter 216. The membrane filter 216 may be, for example, a Perforene™ filter as produced by Lockheed Martin. This type of filter is capable of separating salts from water in the above-described cooling agent composition for remixing that is later to occur. The membrane filter 216 may include, for example, a perforated graphene sheet supported by a backing sheet 220. In the arrangement shown, deionized water 222 passes through the membrane filter 216 and into line 224. Salt concentrates exit through line 226 under control of valve 228. The salt concentrates may be optionally subjected to a drying unit 230 for more complete drying. This drying unit may be, for example, solar powered, an open air system or one that undergoes the application of heat energy from hydrocarbon fuels. The finished salt concentrates 232 may be conveyed to cooler 234, which is used for purposes described above, then with recycle through line 236 for resupply of salt water 206 in a closed process loop. Alternatively, the recycle may be supplied as salt water 208.

Figure 3:
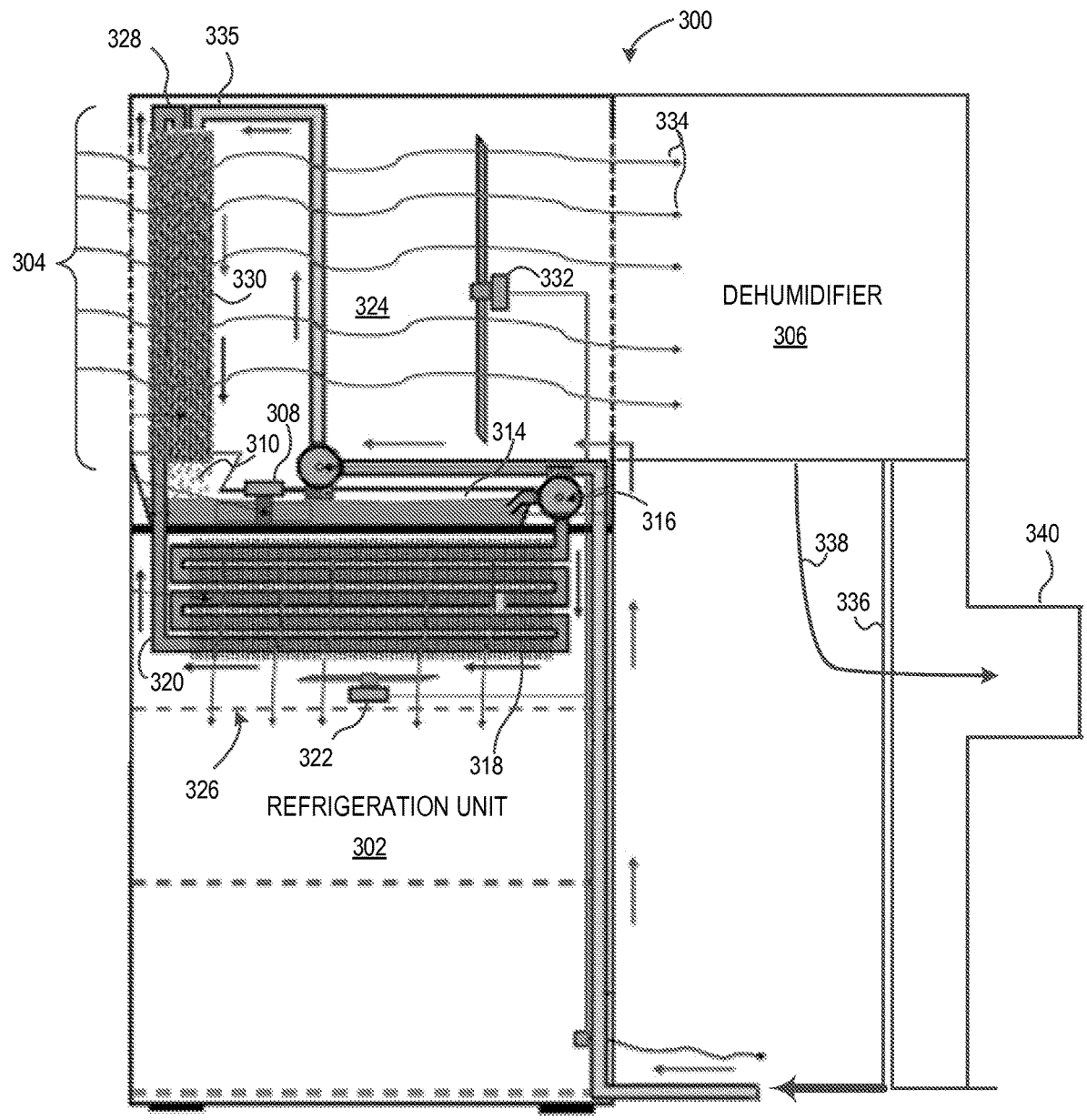
FIG. 3 shows a cooling system utilizing the endothermic action of a cooling agent composition according to one embodiment.

FIG. 3 shows a forced air cooling system 300, which is formed of a refrigeration unit 302, an evaporative cooling unit 304, and an optional dehumidifier unit 306. A mixer 308 blends a crystallized form of the cooling agent composition 310 with water provided from the dehumidifier unit 306, as described in more detail below. The mixture provides endothermic action where, for example, the crystallized cooling agent composition may provide cooling to the effect of 130 Btu/lb when mixed with water, or another level of cooling depending upon the selected salts. Mixer 308 provides the liquid coolant n mixture to coolant basin 314. A circulating pump 316 circulates the cold liquid mixture from coolant basin 314 through refrigeration coils 318 and then into the evaporative cooling unit 304 through return line 320. A fan 322 circulates air from chamber 324 through coils 318 for provision of cool air 326 to the refrigeration unit 302.

The return line 320 discharges 328 onto an evaporative support, such as an evaporative cooling pad 330. Fan 332 pulls air 334 across the evaporative cooling pad 330. The evaporative cooling pad 330 is sized to crystallize salts in the water (or other solvent) from discharge 328. The crystallization may be partial or substantially complete. Where, for example, the dried salt composition applied to mixer 308 provides an endothermic effect of 130 Btu/lb, the crystallization on evaporative pad 330 now provides the opposite effect in the amount of 130/lb. This is compensated by the evaporative cooling effect of water volatilizing on the evaporative cooling pad 330. The enthalpy of vaporization of water provides about 970 Btu/lb of water, which overwhelms the heating effect as the salt crystallizes.

Salts crystallizing on the evaporative cooling pad 330 will eventually clog the pad to impede the flow of air 334 into chamber 324. Periodically then, at time intervals as needed to avoid such clogging, deionized water from a second discharge 334 may be used to clean the evaporative cooling pad 330. A mechanical actuator, such as a roller (not depicted), may be used to enhance solvolysis and/or dislodgement of crystalline salts from the evaporative cooling pad 330. The materials released from the evaporative cooling pad and associated water fall as salt material 310 into coolant basin 314 of the refrigeration unit 302.

The air 314 in chamber 324 is accordingly cooled and the water content of air 314 is increased by the evaporation process. This cool moist air enters dehumidifier 306. As is known in the art, dehumidifiers may operate on a variety of principles. By way of example, these include mechanical or refrigerative dehumidifiers that drawn air over a refrigerated coil, Peltier heat pumps, adsorption desiccants, and ionic membranes. A preferred form of dehumidifier 306, according to one embodiment, is a membrane compressed air dryer, such as may be purchased on commercial order and the HMD™ or HMM Sweepsaver™ products from SPX/Hankinson International of Ocala Fla. In this type of system, as is known in the art, compressed air may be filtered through a coalescing filter to remove piqued water droplets. The air then passes internally through a system of hollow fibers in one or more membrane bundles. Simultaneously, a portion of dried air is directed over the exterior surfaces of the fibers. To sweep water vapor that has penetrated the fiber membrane. The sweep air absorbs water from the membrane and may be discharged from the system. Alternatively, as depicted in FIG. 3, water drips from the external surfaces and is collected for discharge through recycle line 336. Cool dry air blows through vent 340 and may be used, for example, to cool a house, a data center, a computer room, an operating room, vending machine, or a manufacturing facility. The dehumidifier unit 306 is optional because it will not be necessary or desirable in all instances to dehumidify the air exiting chamber 324.

Figure 4:
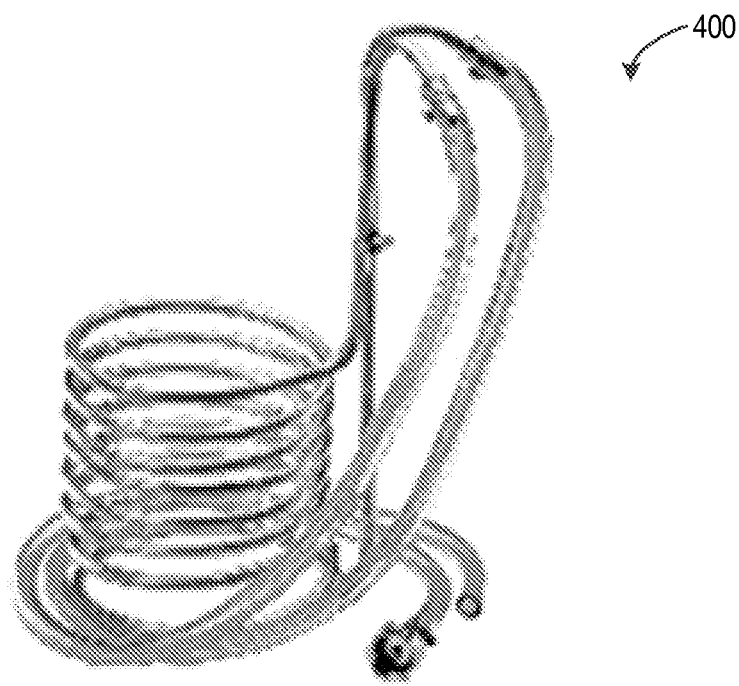
FIG. 4 shows refrigeration coils that may be used in a cooling system such as that shown in the embodiment of FIG. 3.
Figure 5:
FIG. 5 shows solar panels that may be cooled using refrigeration coils compatible with the embodiment of FIG. 3

The parts of forced air cooling system 300 may be constructed for application-specific uses. By way of example, the refrigeration coils 318 may be specially constructed for niche applications, for example, as shown in FIG. 4. Coils 400 are specially constructed to fit around the bearings of a wind turbine generator. The coils may also have a flattened configuration for use in cooling solar panels 500. In the solar panel application, the excess solar heat advantageously assists in drying salts of the cooling agent composition.

Figure 6:
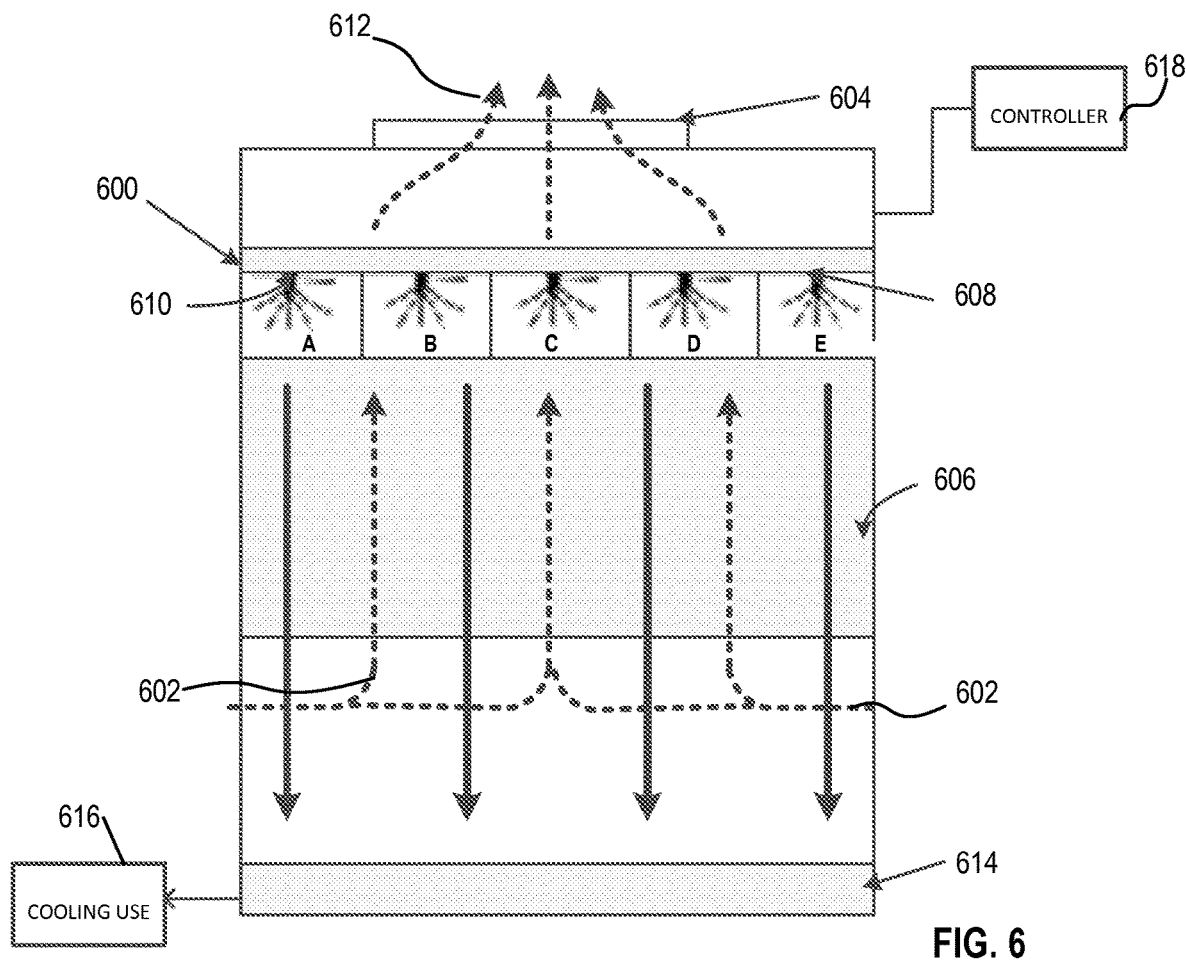
FIG. 6 shows a cooling tower utilizing the endothermic action of a cooling agent composition according to one embodiment.

FIG. 6 is a mid-sectional view of a counter-flow cooling system 600 that may be used as an industrial cooling tower. Dry air 602 enters the system as pulled by fan 604. The dry air 602 passes through a fill material 606 that is wet by the action of spray nozzles 608, 610. This converts the dry air 602 into warm moist air 612. Excess liquid from spray nozzles 608, 610 collects in basin 614 after passing through the fill material 606, having been chilled by the action of water evaporating in the fill material. This liquid is applied to a cooling use 616, such as the cooling of a building, a nuclear reactor, or an electrical generation plant.

The cooling effect is enhanced by use of the cooling agent composition as described above. The cooling agent is contained in the water emanating from nozzles 608, 610. The spray pattern onto fill material 606 is divided into zones, such as zones A, B, C, D and E. Each zone is allocated a corresponding water source, such as nozzle 610 is allocated to zone A. The nozzles for each zone are selectively activated, for example, under the direction of controller 618, by providing periodic spray bursts or continuous low volume spray, to facilitate drying of the cooling agent composition with resultant salt crystallization on the fill material 606. Then the nozzles may be activated to flush one or more zones to achieve endothermic action by solvolysis of the crystallized salt material. This reduces the temperature of water or other liquid that is collected in the collection basin 614 and applied to cooling use 616. The manner of operation directed by controller 618 may be determined, for example, according to a multivariate correlation relating temperature, air moisture content, salt content, type of salt, time of application, and air flow rate to a desired level of crystallization as determined by empirical data in the intended environment of use. Not all of these variables will be necessary for this correlation, but a plurality of these variables is preferred. Other models relating these variables, such as a neural network or adaptive filter may also be used.

Figure 7:
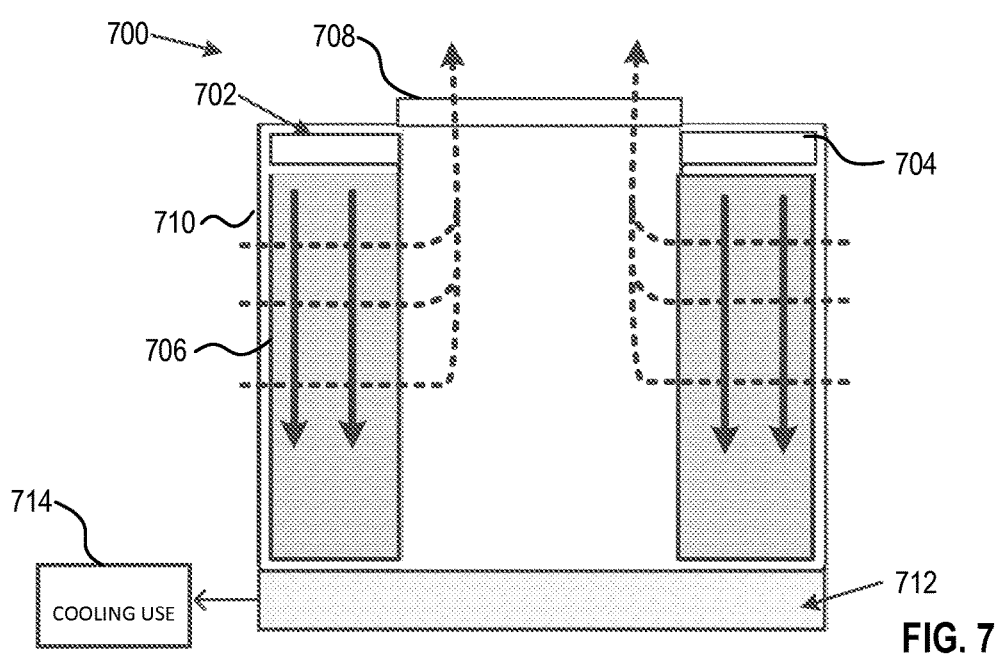
FIG. 7 shows a cooling tower utilizing the endothermic action of a cooling agent composition according to one embodiment.

FIG. 7 is a mid-sectional view of a crossflow cooling system 700. In this system, hot water 702 enters a distribution basin 704 that controls distribution of water to fill material 706. Fan 708 pulls dry air external across the fill material 706, which is wet with water from the distribution basin 704. This provides evaporative cooling of the water, which passes through fill material 710 under the influence of gravity into collection basin and is delivered to cooling use 714.

The cooling effect is enhanced by use of the cooling agent composition as described above. The cooling agent is contained in the water emanating from distribution basin 704. As shown in FIG. 8, the distribution basin 704 includes a reservoir 800 for collecting hot water. The reservoir 800 is drained by selective activation of valves 802, 804, 806, 808, which are electronically opened and closed as determined by controller 810. As above, each valve is allocated to a corresponding zone (not depicted) located in the filler material 706 beneath the distribution basin 704. The manner of delivery facilitates drying of cooling agent composition in the water with resultant salt crystallization on the fill material 704. Then respective valves of the distribution basin may be activated to flush one or more zones to achieve endothermic action by solvolysis of the crystallized salt material. This reduces the temperature of water or other liquid that is collected in the collection basin 712 and applied to cooling use 714.

The manner of operation directed by controller 810 may be determined, for example, according to a multivariate correlation relating temperature, air moisture content, salt content, type of salt, time of application, and air flow rate to a desired level of crystallization as determined by empirical data in the intended environment of use. Not all of these variables will be necessary for this correlation, but a plurality of these variables is preferred. Other models relating these variables, such as a neural network or adaptive filter may also be used.

FIG. 9A shows a cold pack 900 formed of thermosealed plastic 902 that defines a water pouch 904 and a salt pouch 906. The salt material within salt pouch 906 is a cooling agent composition as described above. A divider 908 separates the water pouch 904 from the salt pouch 906. The divider 908 forms a comparatively weak seal as compared to a perioral seal, such as by being thinner and so also weaker. Either water pouch 904 or salt pouch 906 may be manually squeezed to rupture the divider 908 for mixing of water and salt. FIG. 9B shows the cold pack 900 after activation in this manner, with mixture 910 providing an endothermic reaction for cooling purposes. This cold pack may be used for medical applications, or in the cooling of food and beverage products.

It will be appreciated that cooling is a function of variables including time. Thus, if salts of the cooling agent composition dissolve too slowly over time, the net cooling effect upon a target object may not be as great as it could be if the salts were to dissolve all at once. It has been discovered that the salt materials dissolve more quickly if a minor amount of water is present with the crystallized salt material. Thus for example, for 1% to 5% by weight of water may be premixed with the salt material to speed solvolysis upon the further addition of water. The amount of water is preferably from 2% to 3% by weight. Thus, the salt material in pouch 906 may have the consistency of a wet sand material. The premix with water does reduce somewhat the endothermic capacity of the salt material, but in many applications results in greater effective cooling by increasing the speed of solvolysis.

Figure 10:
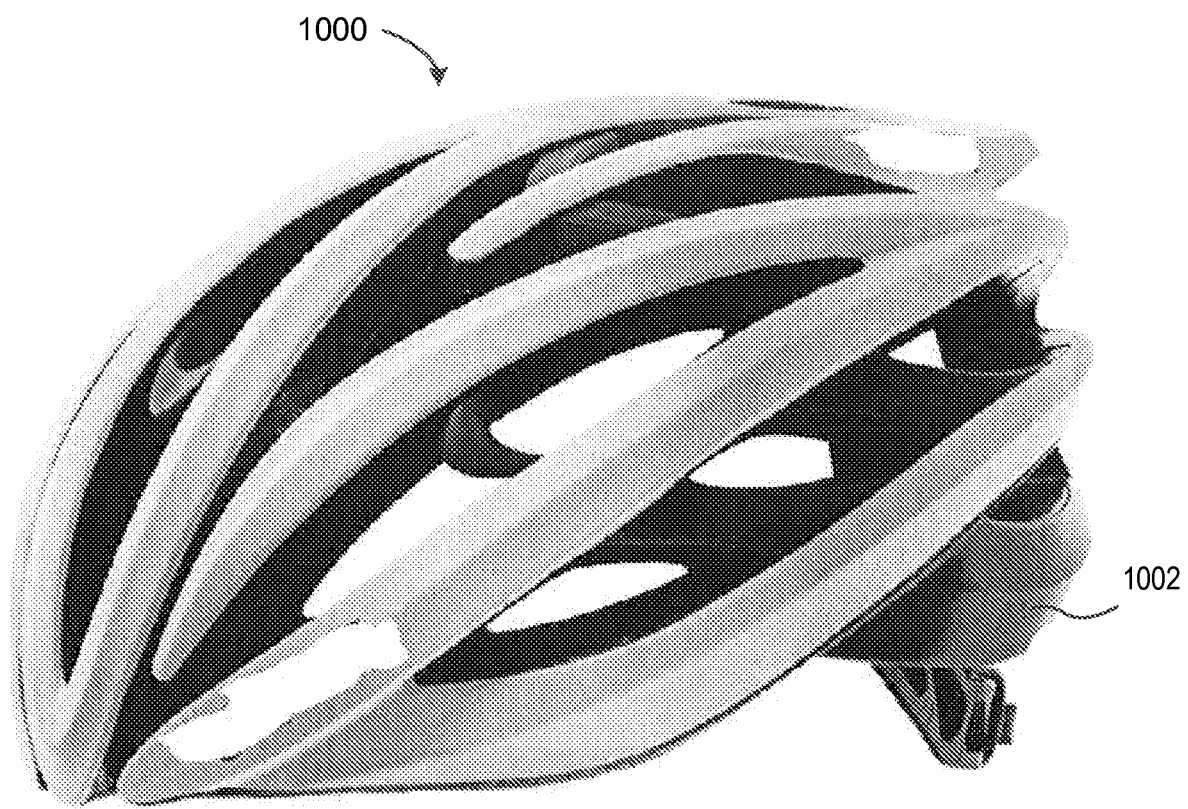
FIG. 10 is an embodiment of a bicycle helmet with a pouch for receipt of a cold pack.

The cold pack 900 is not limited to the shape shown in FIGS. 9A and 9B. This structure may be fashioned into a joint wrap, such as a knee or ankle wrap, a head wrap, neck wrap, or shoulder wrap. These devices may be constructed of hollow materials to provide an integral reservoir for retention of the cooling agent composition when mixed as a liquid or, alternatively, the cold pack 900 may be placed into a pouch within these articles of clothing. By way of example, FIG. 10 shows a bicycle helmet 1000 with a pouch 1002 for receipt of cold pack 900. The cold pack 900 does not require divider 908 and may be made to accept the cooling agent composition in crystallized form to which water may be added and sealed for retention by use of a threaded cap or other closure. The location of pouch 1002 is at the back of the neck, but other locations may be used, such as any contact point that may protect the skull in the manner of a water helmet. Bicycle helmets of the prior art are usually filled with styrofoam materials, as is well known, but accordant to the present instrumentalities the styrofoam is replaced with a bladder for retention of a cooling agent composition that is selectively mixed with water to cool the head while cycling.

Again, as to any of the foregoing embodiments, the cooling agent composition may be provided as a fertilizer blend with NPK content for an intended purpose. Thus, if the salt of the cooling agent composition needs renewal, it is a simple matter to dispose of the old salts by using them as a fertilizer, such as a spray fertilizer. A particularly preferred form of the cooling agent composition for many such uses is ammonium nitrate that has been stabilized against detonation by the addition of phosphate material, such as from 3% to 8% by weight phosphate. To this may be added additional salts to provide a desired NPK blend, such as a 14-7-7 or 12-12-12 blend. However, it is desirable to keep the ammonium nitrate content high, for example, as more than 50% or more than 80% of the composition by weight due to the excellent endothermic capacity of ammonium nitrate, together with the relatively low toxicity of this material.

It is thus apparent that the compositions of the present invention accomplish the principal objectives set forth above. Various modifications may be made without departing from the spirit and scope of the invention.

We claim:

1. A wearable cold pack comprising:
   a wearable article of clothing formed with a reservoir for retention of liquid, and
   a cooling agent composition including a salt that is a co-milled blend of at least 100 mesh particle size of about 50 to 95 parts ammonium nitrate, about 1 to 10 parts ammonium phosphate to stabilize against detonation, about 4 to 30 parts potassium compound, about 1 part carbon containing compounds and mixed with about 90 parts water in the reservoir, the salt having a capacity to provide an endothermic effect to enhance cooling when mixed with water, wherein after achieving temperature equilibrium with the surrounding environment, the cooling agent composition is recyclable as a balanced NPK fertilizer.

2. The wearable cold pack of claim 1, constructed and arranged as an article selected from the group consisting of a joint wrap, head wrap, neck wrap, a helmet and a shoulder wrap.

3. The wearable cold pack of claim 1, wherein the cooling agent composition in substantially complete crystalized form is capable of cooling in the amount of at least 130 Btu/lb due to endothermic effect when mixed with water.

* * * * *